United States Patent [19]

Guanasekera

[11] Patent Number: 4,749,787

[45] Date of Patent: Jun. 7, 1988

[54] PROCESS OF ISOLATING VINBLASTINE FROM THE PLANT CATHARANTHIS ROSEUS

[75] Inventor: Sarath P. Guanasekera, Vero Beach, Fla.

[73] Assignee: Harbor Branch Oceanographic Institution, Inc., Ft. Pierce, Fla.

[21] Appl. No.: 922,514

[22] Filed: Oct. 23, 1986

[51] Int. Cl.$^4$ .......................................... C07D 519/04
[52] U.S. Cl. .................................................. 540/478
[58] Field of Search ......................... 540/478; 514/283

[56] References Cited

U.S. PATENT DOCUMENTS

| | | | |
|---|---|---|---|
| 3,097,137 | 7/1963 | Beer et al. | 514/183 |
| 3,205,220 | 9/1965 | Svoboda et al. | 514/283 |
| 3,370,057 | 2/1968 | Svoboda et al. | 540/478 |
| 3,932,417 | 1/1976 | Jones | 540/478 |
| 4,172,077 | 10/1979 | Jovánovics et al. | 540/478 |
| 4,203,898 | 5/1980 | Cullinan et al. | 540/478 |
| 4,209,443 | 6/1980 | Jovánovics et al. | 540/478 |

FOREIGN PATENT DOCUMENTS 0653005  11/1962  Canada ................. 540/478

OTHER PUBLICATIONS

Ciulei, Chemical Abstracts, vol. 71, 128620k (1969).
Renaudin, Chemical Abstracts, vol. 103, 210185k (1985).

Primary Examiner—Donald G. Daus
Assistant Examiner—Diana G. Rivers
Attorney, Agent, or Firm—Carroll F. Palmer

[57] ABSTRACT

This invention relates to a chemical process of producing an antitumor alkaloid. More particularly, it relates to a method of isolation of vinblastine from *Catharanthus roseus*, comprising the steps of: extracting *C. roseus* leaves with an acidified aqueous solution; raising the pH and extracting an alkaloid mixture with an organic solvent; chromatographing a solution of the alkaloid mixture over dextran and silica gel columns to obtain vinblastine containing fractions for isolation.

13 Claims, No Drawings

PROCESS OF ISOLATING VINBLASTINE FROM THE PLANT CATHARANTHIS ROSEUS

FIELD OF THE INVENTION

This invention relates to a new process for producing an organic compound which has useful antitumor activity. More particularly, this invention relates to an improved method for the isolation of vinblastine from the plant, *Catharanthus roseus*.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. Malignant tumors inflict mammals and man with a variety of disorders and conditions including various forms of cancer and leukemia. The seriousness of cancer is well known, e.g., cancer is second only to heart and vascular diseases as a cause of death in man.

Several naturally-occuring alkaloids have been found active in the treatment of experimental malignancies in animals. Among these are vinblastine and vincristine which are now marketed as drugs for the treatment of malignancies, particularly the leukemias and related diseases in humans.

Isolation of vinblastine from the *Catharanthus roseus* plant is disclosed, for example, by the following patents:

U.S. Pat. No. 3,205,220 to Svoboda et al. discloses a process for extracting vinblastine utilizing hexane to initially defat the roseus plants and extraction of vinblastine from the plant with 2% tartaric acid and portions of benzene.

U.S. Pat. No. 4,203,898 to Cullinan et al. discloses utilizing benzene as a water immiscible solvent for extracting vinca alkaloids from the *Catharanthus roseus* plant, the benzene solvent is combined with an aqueous acidic extract which is then adjusted to a pH of 6 or 7. An optional gel exclusion filtration step is disclosed utilizing a cross-linked dextran gel (Sehadex G-25F) in a citrate buffer system.

U.S. Pat. No. 3,932,417 to Jones discloses a method for preparing vinca alkaloids utilizing an aqueous acid solution and benzene as preferred extracting solvents and also discloses that other water immiscible solvents may be used in place of benzene (e.g. toluene). Jones utilizes a citrate buffer as part of the optional gel exclusion purification step.

U.S. Pat. No. 4,172,077 to Jovanics et al. broadly discloses extraction of vinca alkaloids from roseus plants with various solvents including a mixture of a lower alkanol and dilute aqueous acid and purification of the alkaloids by phase-change methods.

While these references disclose various methods for isolating vinca alkaloids further methods which may involve simpler procedures and/or higher yields are desirable.

SUMMARY OF THE INVENTION

It is therefore an object of the invention to provide a novel process for producing a high yield of vinblastine and salts thereof which are useful as antitumor agents.

Additional objects and advantages of the invention will be set forth, in part, in the description which follows and in part will be obvious from this description, or may be learned by the practice of the invention. The objects and advantages of the invention are realized and obtained by means of the processes and the combinations particularly pointed out in the appended claims.

To achieve the objects in accordance with the purposes of the invention, as embodied and fully described herein, the invention comprises a process to prepare vinblastine or its salts such as, vinblastine sulfate. The process comprises the steps of extracting *Catharanthus roseus* plant with water acidified with a dilute acid to a pH in the range of from 3 to 4 and forming an aqueous phase extract comprising an alkaloid mixture thereof; adding a concentrated base to raise the pH of the aqueous extract to a pH in the range of from 6 to 7; extracting the aqueous phase extract with a first organic solvent to obtain a vinblastine extract; subjecting the first organic solvent extract to evaporation to give a residue of an alkaloid mixture; dissolving the alkaloid mixture in a second organic solvent to form an alkaloid solution; chromatographing the alkaloid solution over dextran on a column with a third organic solvent eluent and obtaining fractions thereof; identifying at least one vinblastine containing fraction; dissolving a vinblastine containing fraction in a fourth organic solvent to form a solution thereof; chromatographing the solution on a column of deactivated silica gel eluted with a fifth organic solvent and obtaining fractions thereof; identifying at least one fraction containing vinblastine; evaporating the vinblastine containing fraction to form a vinblastine residue; dissolving the vinblastine residue in an anhydrous alcohol at room temperature; adjusting the pH of the solution to about 4 with a 2% anhydrous acid solution; allowing crystals of the vinblastine composition to form; and harvesting the vinblastine composition formed by filtration.

In preferred embodiments of the invention the dilute acid is selected from the group consisting of acetic acid, HCl and $H_2SO_4$; the concentrated base is selected from the group consisting of $NH_4OH$, KOH and NaOH; the first and fourth organic solvents are selected from the group consisting of $CH_2Cl_2$, $CHCl_3$, $CCl_4$ and ethyl acetate; the second, third and fifth organic solvents are mixtures of varying proportions of $CH_2Cl_2$, $CHCl_3$, $CCl_4$ or ethyl acetate, and methanol: the anhydrous alcohol is anhydrous ethanol, propanol or isopropanol; and the 2% anhydrous acid solution is 2% sulfuric acid in dry ethanol, propanol or ispropanol.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, an example of which is illustrated in the following example section.

The invention comprises a process to prepare vinblastine compositions including salts thereof. The process comprises the steps of extracting *Catharanthus roseus* plant with water acidified with a dilute acid to a pH in the range of from 3 to 4 and forming an aqueous phase extract comprising an alkaloid mixture thereof; adding a concentrated base to raise the pH of the aqueous extract to a pH in the range of from 6 to 7; extracting the aqueous phase extract with a first organic solvent to obtain a vinblastine extract; subjecting the first organic solvent extract to evaporation to give a residue of an alkaloid mixture; dissolving the alkaloid mixture in a second organic solvent to form an alkaloid solution; chromatographing the alkaloid solution over dextran on a column with a third organic solvent eluent and obtaining fractions thereof; identifying at least one vinblastine containing fraction; dissolving a vinblastine containing fraction in a fourth organic solvent to form a solution thereof; chromatographing the solution on a column of deactivated silica gel eluted with a fifth organic solvent and obtaining fractions thereof; identifying at least one fraction containing vinblastine; evaporating the vinblastine containing fraction to form a vinblastine residue; dissolving the vinblastine residue in a minimal amount of an anhydrous alcohol at room temperature; adjusting the pH of the solution to about 4 with a 2% anhydrous acid solution; allowing vinblastine crystals to form; and harvesting the vinblastine crystals formed by filtration.

In preferred embodiments of the invention the dilute acid is selected from the group consisting of acetic acid, HCl and $H_2SO_4$; the concentrated base is selected from the group consisting of $NH_4OH$, KOH and NaOH; the first and fourth organic solvents are selected from the group consisting of $CH_2Cl_2$, $CHCl_3$, $CCl_4$ and ethyl acetate; the second, third and fifth organic solvents are mixtures of $CH_2Cl_2$, $CHCl_3$, $CCl_4$ or ethyl acetate, and methanol; the anhydrous alcohol is anhydrous ethanol, propanol or isopropanol; and the 2% anhydrous acid solution is 2% sulfuric acid in dry ethanol, propanol or isopropanol.

A detailed description and explanation of a preferred embodiment of the process to produce vinblastine sulfate is as follows: *Catharanthus roseus* is extracted using water acidified to pH of 3–4 with dilute acetic acid. The aqueous extract is then raised to a pH of 6 to 7 by adding concentrated $NH_4OH$ thereto. The aqueous phase is then extracted with $CH_2Cl_2$ and evaporated in vacuo to give an alkaloid mixture residue. A portion of the alkaloid mixture is dissolved in a mixture of $CH_2Cl_2$ and MeOH and filtered. The filtrate is chromatographed over dextran particularly, SEPHADEX LH-20 which is a hydroxypropylated cross-linked dextran with bead size of from 25 to 100 microns. The fractions are identified as containing vinblastine by chromatography methods. A portion of the vinblastine containing fraction is dissolved in $CH_2Cl_2$ and chromatographed on a column of silica gel to produce fractions containing vinblastine as identified by thin layer chromatography. The combined fractions containing vinblastine are evaporated to dryness under vacuo to afford an alkaloid fraction which is dissolved in anhydrous ethanol. The pH of the solution is adjusted to 4.0 with 2% ethanolic sulfuric acid. The solution is allowed to stand overnight in a refrigerator and the vinblastine sulfate formed is harvested by filtration.

While $CH_2Cl_2$ and $CH_2Cl_2$/MeOH mixtures are the presently preferred choice for solvents, other suitable solvents may be substituted. Suitable solvents which may be substituted for $CH_2Cl_2$ include, but are not limited to, the following organic solvents: $CHCl_3$; $CCl_4$; and ethyl acetate. Suitable solvents which may be substituted for MeOH include other lower alkanols such as butanol or propanol.

Any suitable fractionation and isolation technique may be utilized in accordance with the invention. Suitable fractionation techniques include various chromatography techniques such as, medium pressure liquid chromatography with a suitable column, as would be known to those skilled in the art, including silica gel, SEPHADEX LH-20; ammonia-treated silica gel; RP-C18, RP-C8, and LICHROSORB $NH_2$ packed columns. These columns are eluted with suitable eluents such as: $CH_2Cl_2$; methanol; mixtures of $CH_2Cl_2$, $CHCl_3$, $CCl_4$ or ethyl acetate, and methanol; and mixtures of $NH_4OH$, methanol and $CH_2Cl_2$.

EXAMPLE

The invention will now be illustrated by an example. The example is not intended to be limiting of the scope of the present invention. In conjunction with the detailed and general description above, the example provides further understanding of the present invention and outlines the process of the invention for producing vinblastine compositions including salts thereof.

The following example represents a preferred embodiment of the invention for satisfying the stated objects of the invention. The starting materials and reagents in the example whose method of preparation are not indicated are commercially available from sources known to the art such as chemical supply houses.

EXAMPLE 1

Preparation Of Vinblastine Sulfate

Freshly harvested partially dried *Catharanthus roseus* stems with leaves and flowers (2.2 kg) were extracted two times successively for 39 hours and 5 days using 12 L of water acidified to pH of about 3–4 with dilute acetic acid. The aqueous extracts were then raised to a pH of about 6 to 7 by adding concentrated $NH_4OH$. The aqueous phase was then extracted with $CH_2Cl_2$ and evaporated in vacuo on a water bath at 30° to give as a residue, 7.9 g of an alkaloid mixture. A portion of the alkaloid mixture (4.2 g) was dissolved in 10 ml mixture of 1:1 $CH_2Cl_2$ and MeOH and filtered through a sintered glass funnel. The filtrate was chromatographed over dextran (Sephadex $LH_{20}$) in a 4.2×50 cm glass column. A mixture of 1:1 $CH_2Cl_2$ and MeOH was used as the mobile phase and 6 fractions collected.

The fractions were identified as containing vinblastine by thin layer chromatography by heating the plate after spraying with 5% vanillin in concentrated $H_2SO_4$. A portion of the vinblastine containing fraction (700 mg) was dissolved in 2 ml of $CH_2Cl_2$ and chromatographed on a column of 30 g of deactivated silica gel. Silica gel (30 g of Kieselgel 60, 230–400 mesh, Merck) was deactivated by adding a mixture of 2 ml of $NH_4OH$ in 15 ml of methanol and 150 ml of $CH_2Cl_2$. The deactivated silica gel slurry was then packed in a glass column 2.5×16 cm and the column was then washed with a column length of $CH_2Cl_2$ to remove MeOH from the column. The column was eluted with 1%, 2%, 3% and 10% mixtures of MeOH-$CHCl_3$ and 24 fractions collected. The fractions were identified as containing vinblastine by thin layer chromatography as above.

Evaporation to dryness under vacuo of the combined fractions containing vinblastine afforded 107.0 mg of alkaloid. The alkaloid fraction was dissolved in 5.0 ml of anhydrous ethanol at room temperature. The pH of the solution was adjusted to about 4.0 with 2% ethanolic sulfuric acid. The solution was allowed to stand overnight in the refrigerator and the vinblastine sulfate formed was harvested by filtration. Weight of the vinblastine sulfate thus obtained was 65.5 mg.

The scope of the present invention is not limited by the description, examples, and suggested uses herein and modifications can be made without departing from the spirit of the invention. For example, it may be noted that other materials and methods such as various chromatographic techniques, eluents and phase materials as known presently or prospectively by those skilled in the art may be useful in accordance with the present invention. Further, other vinca alkaloids such as vincristine may be prepared utilizing the method of the invention. Thus, it is intended that the present invention cover the modifications and variations of this invention provided they come within the scope of the appended claims and their equivalents

What is claimed is:

1. A process for preparing vinblastine compositions comprising the steps of:
    extracting Catharanthus roseus plant with water acidified with a dilute acid selected from the group consisting of acetic, hydrochloric and sulfuric acid to a pH in the range of from 3 to 4 and forming an aqueous phase extract comprising an alkaloid mixture thereof and next adding a concentrated base selected from the group consisting of ammonium hydroxide, potassium hydroxide, and sodium hydroxide to raise the pH of the aqueous extract to a pH in the range of from 6 to 7;
    extracting the aqueous phase extract with a first organic solvent selected from the group consisting of methylene chloride, cloroform, carbon tetrachloride and ethyl acetate to obtain a vinblastine extract;
    subjecting said organic solvent extract to evaporation to give a residue of an alkaloid mixture;
    dissolving the alkaloid mixture in a second organic solvent selected from the group consisting of any one of methylene chloride, chloroform, carbon tetrachloride, and ethyl acetate in a 1:1 mixture with methanol to form an alkaloid solution;
    chromatographing the alkaloid solution over dextran on a column with a third organic solvent eluent selected from the group consisting of any one of methylene chloride, chloroform, carbon tetrachloride and ethyl acetate in a 1:1 mixture with methanol and obtaining fractions thereof;
    identifying at least one vinblastine containing fraction;
    dissolving a vinblastine containing fraction in a fourth organic solvent selected from the group consisting of methylene cloride, chloroform, or carbon tetrachloride and ethyl acetate to form a solution thereof;
    chromatographing the solution on a column of deactivated silica gel eluted with a fifth organic solvent selected from the group consisting of 1 to 10% mixtures of methanol in methylene chloride, chloroform, carbon tetrachloride, and ethyl acetate and obtaining fractions thereof;
    identifying at least one fraction containing vinblastine;
    evaporating the vinblastine containing fraction to form a vinblastine residue;
    dissolving the vinblastine residue in an anhydrous alcohol at room temperature;
    adjusting the pH of the solution to about 4.0 with a 2% anhydrous acid solution;
    allowing the vinblastine compositions to form crystals; and
    harvesting the vinblastine composition formed by filteration.

2. A process according to claim 1 wherein the dilute acid is acetic acid.

3. A process according to claim 1 wherein the concentrated base is $NH_4OH$.

4. A process according to claim 1 wherein the first organic solvent and fourth organic solvent is $CH_2Cl_2$.

5. A process according to claim 1 wherein the second organic solvent and the third organic solvent eluent are a 1:1 mixture of $CH_2Cl_2$ and methanol.

6. A process according to claim 1 wherein the fifth organic solvent is 1% to 10% mixtures of MeOH in $CH_2Cl_2$.

7. A process according to claim 1 wherein the anhydrous alcohol is selected from the group consisting of anhydrous ethanol, propanol, and isopropanol.

8. A process according to claim 1 wherein the 2% anhydrous acid solution is 2% sulfuric acid in dry ethanol, propanol or isopropanol.

9. A process according to claim 1 wherein medium pressure liquid chromatography method is substituted for the usual gravity column method.

10. A process according to claim 1 wherein the dextran is hydroxypropylated cross-linked dextran.

11. A process according to claim 1 wherein the vinblastine composition produced is a salt of vinblastine.

12. A process according to claim 1 wherein the salt is vinblastine sulfate.

13. A process for preparing vinblastine sulfate comprising the steps of:
    extracting Catharanthus roseus plant with water acidified with a dilute acid to a pH in the range of from 3 to 4 and forming an aqueous phase extract comprising an alkaloid mixture thereof and next;
    adding concentrated $NH_4OH$ to raise the pH of the aqueous extract to a pH in the range of from 6 to 7;
    extracting the aqueous phase extract with $CH_2Cl_2$ to obtain a vinblastine extract;
    subjecting said organic solvent extract to evaporation to give a residue of an alkaloid mixture;
    dissolving the alkaloid mixture in 1:1 mixture of $CH_2Cl_2$ and MeOH to form an alkaloid solution;
    chromatographing the alkaloid solution over a column packed with hydroxypropylated cross-linked dextran eluted with a 1:1 mixture of $CH_2Cl_2$ and MeOH and obtaining fractions thereof;
    identifying at least one vinblastine containing fraction by thin layer chromatography;
    dissolving a vinblastine containing fraction in $CH_2Cl_2$ to form a solution thereof;
    chromatographing the solution on a column of deactivated silica gel eluted with a 1% to 10% mixture of MeOH in $CHCl_3$ and obtaining fractions thereof;
    identifying at least one fraction containing vinblastine by thin layer chromatography;
    evaporating the vinblastine containing fraction to form a vinblastine residue;
    dissolving the vinblastine residue in anhydrous ethanol at room temperature;
    adjusting the pH of the solution to about 4.0 with a 2% anhydrous ethanolic sulfuric acid solution; and
    harvesting the vinblastine sulfate formed by filtration.

* * * * *